US008133289B2

(12) United States Patent
Gruter et al.

(10) Patent No.: US 8,133,289 B2
(45) Date of Patent: Mar. 13, 2012

(54) METHOD FOR THE SYNTHESIS OF 5-ALKOXYMETHYL FURFURAL ETHERS AND THEIR USE

(75) Inventors: Gerardus Johannes Maria Gruter, Heemstede (NL); Frits Dautzenberg, San Diego, CA (US)

(73) Assignee: Furanix Technologies B.V., Amsterdam (NL)

( * ) Notice: Subject to any disclaimer, the term of this patent is extended or adjusted under 35 U.S.C. 154(b) by 96 days.

(21) Appl. No.: 12/282,264

(22) PCT Filed: Mar. 12, 2007

(86) PCT No.: PCT/EP2007/002145
§ 371 (c)(1),
(2), (4) Date: Dec. 17, 2008

(87) PCT Pub. No.: WO2007/104514
PCT Pub. Date: Sep. 20, 2007

(65) Prior Publication Data
US 2009/0131690 A1 May 21, 2009

(30) Foreign Application Priority Data
Mar. 10, 2006 (EP) .................................... 06075564

(51) Int. Cl.
*C07D 307/48* (2006.01)
*C10L 1/185* (2006.01)
*C07D 307/02* (2006.01)

(52) U.S. Cl. .......... 44/351; 549/488; 549/489; 549/483; 44/350

(58) Field of Classification Search .................. 549/489, 549/483, 488; 44/350, 351
See application file for complete search history.

(56) References Cited

U.S. PATENT DOCUMENTS

| 3,290,263 | A | * | 12/1966 | Smythe et al. ................. 527/303 |
| 4,464,204 | A | * | 8/1984 | Niekamp et al. ................ 127/36 |
| 5,616,631 | A | | 4/1997 | Kiuchi et al. |
| 7,317,116 | B2 | * | 1/2008 | Sanborn ........................ 549/483 |

FOREIGN PATENT DOCUMENTS

| DE | 635 783 | 9/1936 |
| DE | 36 21 517 A1 | 1/1988 |
| FR | 2 723 945 A1 | 3/1996 |
| JP | 60-028970 A | 2/1985 |
| RU | 2 203 279 C1 | 4/2003 |
| WO | WO 99/67409 A1 | 12/1999 |
| WO | 2006/063220 A2 | 6/2006 |

OTHER PUBLICATIONS

XP-002385430, Tarabanko, V.E., et al., "Preparation of butyl levulinate by the acid-catalzyed conversion of sucrose in the presence of butanol", Khimiya Rastitel'nogo Syr'ya, (2), 3-37, (2004).
XP-002385431, Tarabanko, V.E., et al., "Catalyzed carbohydrate dehydration in the presence of butanol at moderate temperatures", Khimiya Rastitel'nogo Syr'ya, (2), 5-15, (2002).
XP-002385647, English abstract for RU 2 203 279.
Garves, K., "Acid catalyzed degradation of cellulose in alcohols", Journal of Wood Chemistry and Technology, vol. 8, No. 1, 121-134, (1988).
Moye, C.J., et al., "Reaction of ketohexoses with acid in certain non-aqueous sugar solvents", Journal of Applied Chemistry, vol. 16, 206-208, (1966).
Tyrlik, S., et al., "Selective dehydration of glucose to hydroxyethylfurfural and a one-pot synthesis of a 4-acetylbutyrolactone from glucose and trioxane in solutions of aluminium salts", Carbohydrate Research, vol. 315, 268-272, (1999).
Moore, J.A., et al., "Polyesters Derived from Furan and Tetrahydrofuran Nuclei", Macromolecules, vol. 11, No. 3, 568-573, (1978).
European Search Report dated Aug. 5, 2009 for EP 09 16 4815.
Cottier L. et al.: "Photooxygenation of 5-(hydroxymethyl)-2-furfural derivatives" Bulletin De La Societe Chimique De France, Societe Francaise De Chimie. Paris, France, Jan. 1, 1986, pp. 844-850.
Brown DC W et al.: "Dehydration reactions of fructose in nonaqueous media" Journal of Chemical Technology and Biotechnology, Blackwell Scientific Publications, Oxford, GB, vol. 32, No. 10, Jan. 1, 1982, pp. 920-924.
B.N Kuznetsov, Rossiiskii khimicheskii zhurnal (Zhurnal Rossiiskogo khimicheskogj obschestva im. D.1. Mendeleeva), 2003, t. XLVII, No. 6, s.83-91. (English translation: B.N Kuznetsov, "Production of liquid fuels and their components from woody biomass", Ros. Khim. Zh. (J. of Rus. Mendeleyev Chem. Society), 2003, vol. XLVII, No. 6, pp. 83-91).

* cited by examiner

*Primary Examiner* — Taylor Victor Oh
(74) *Attorney, Agent, or Firm* — Hoffmann & Baron, LLP

(57) ABSTRACT

Method for the manufacture of 5-alkoxymethylfurfural derivatives by reacting a fructose and/or glucose-containing starting material with an alcohol in the presence of a catalytic or sub-stoechiometric amount of solid ("heterogeneous") acid catalyst. The catalysts may be employed in a continuous flow fixed bed or catalytic distillation reactor. The ethers can be applied as a fuel or fuel additive.

2 Claims, 2 Drawing Sheets

000
METHOD FOR THE SYNTHESIS OF 5-ALKOXYMETHYL FURFURAL ETHERS AND THEIR USE

CROSS-REFERENCE TO RELATED APPLICATIONS

This application is the National Stage of International Application No. PCT/EP2007/002145, filed Mar. 12, 2007, which claims the benefit of European Application No. EP 06075564.2, filed Mar. 10, 2006, the contents of which are incorporated by reference herein.

FIELD OF THE INVENTION

The present invention relates to a method for the preparation of derivatives of 5-hydroxymethylfurfural (HMF), in particular ether derivatives of HMF, more in particular to 5-alkoxymethylfurfural ethers and to their application as a fuel or fuel additive.

BACKGROUND OF THE INVENTION

The conversion of sugars or sugar (hexoses) containing biomass into more economically useful compounds is of increasing interest. Current fuel activities are mainly directed towards ethanol from sugar/glucose. Typically, sucrose and glucose are fermented into ethanol. One glucose molecule is converted into two molecules of ethanol and two molecules of $CO_2$. This conversion has drawbacks especially in view of atom economy, the low energy density of ethanol (7.7 kWh/kg or 6.1 kWh/L) and its relative low boiling point (78.4 degrees Celsius).

Another application area involves the conversion of sugars such as fructose into HMF in the presence of an acid catalyst has been reported (for example in EP0230250 to Suedzucker or EP0561928 to CEA)). In this case HMF is obtained as a highly potential starting material for obtaining bio-based monomer such as furandicarboxylic acid which can inter alia be used as an alternative to terephthalic acid as a monomer for polyethylene terephthalate type polyesters (Moreau et. al. in Topics in Catalysis Vol 27, Nos. 1-4, 2004, 11-30 and references cited therein). When under these conditions sucrose or glucose was used as a feed, no conversion to HMF is observed (Moreau et. al. in Topics in Catalysis Vol 27, Nos. 1-4, 2004, p 13, col 2. line 2-3), which is a distinct disadvantage given the low price and abundant availability of sucrose and glucose. Only in the presence of DMSO, DMF and DMA (low HMF yields from glucose: Ishida et. al. Bull. Chem. Soc. Jpn 74 2001, 1145) or in a sub- and supercritical mixture of acetone and water (fructose, glucose, sucrose and inulin conversion to HMF in 77%, 48%, 56% and 78% yields respectively: Vogel et. al. Green Chemistry 5, 2003, 280) reasonable HMF yields from starting materials other than fructose were obtained.

In the current market situation, fructose as feed is undesirable given the high price thereof, compared to glucose and/or sucrose. Therefore, so far, no process for the synthesis of HMF has been developed on an industrial scale.

The synthesis chemistry and applications of HMF are reviewed extensively in Lewkowski, ARKIVOC 2001, (i) 17-54; in Gandini, Prog. Polym. Sci. 22, 1997, 1203; in Lichtenthaler, C. R. Chimie, 7, 2004, 65 and Acc. Chem. Res. 35, 2002, 728; and Moreau, Topics in Catalysis, 27, 2004, 11.

DE3621517 relates to a process for the synthesis of alkoxymethylfurfurals and alkyl levulinates from cellulose or lignocelluloses or starch and alcohols. The starting materials are heated briefly (for 1 to 60 minutes) at 170 DEG to 225 DEG C. with an addition of a strong, catalytically acting acid and, if appropriate, a further, inert solvent in a pressure apparatus. Alcohols which can be employed are primary or secondary aliphatic alcohols, preferably methanol or ethanol. The strong acid used is preferably sulphuric acid at a concentration of 0.5 to 10% (based on the alcohol), if appropriate with an addition of a metal halide. Lignocellulose-based raw materials and waste substances, such as wood, wood pulp (cellulose), waste paper, cereal straw, bagasse or the like, can thus be converted into extractable and distillable organic intermediates. Similar information is provided by the inventor of this German patent reference in JOURNAL OF WOOD CHEMISTRY AND TECHNOLOGY, MARCEL DEKKER, NEW YORK, NY, US-ISSN 0277-3813, Vol: 8, Nr. 1, Page(s): 121-134 (1988). On the other hand, the process produces primarily alkyl levulinates; the production of HMF ethers using the sulphuric acid (a non-solid) is rather poor (the maximum yield of an HMF-ether reported in the 11 examples of DE621517 is 5.3% and 2.7% in Garves' scientific paper).

DE635783 describes a process for the preparation of alkoxymethylfurfurals and alkyl levulinate esters. The acid used is gaseous hydrochloric acid, a non-solid catalyst. As is illustrated in the examples of this German patent, the product prepared from glucose, saccharose, or starch is mostly the alkyl levulinate ester (the maximum yield of EMF ether reported is 6.4%.

Tyrlik et al describes the "Selective dehydration of glucose to hydroxymethylfurfural and a one-pot synthesis of a 4-acetylbutyrolactone from glucose and trioxane in solutions of aluminium salts" in CARBOHYDRATE RESEARCH, ELSEVIER SCIENTIFIC PUBLISHING COMPANY. AMSTERDAM, NL-ISSN 0008-6215, Vol: 315, Nr. 3-4, Page(s): 268-272 (1999). The acidic catalyst under the reaction conditions illustrated in this article is a homogeneous catalyst. The yield of the alkoxymethylfurfural is rather poor (the maximum yield of HMF+HMF-ether combined is 14%.

Moye et al describes the "Reaction of ketohexoses with acid in certain non-aqueous sugar solvents" in JOURNAL OF APPLIED CHEMISTRY, SOCIETY OF CHEMICAL INDUSTRY. LONDON, GB, Vol: 16, Nr. 7, Page(s): 206-208 (1966). HMF is made using various acidic catalysts from fructose, sorbose, kestose and inulin (a group of polysaccharides based on fructose with a terminal glucose group). No experiments were done with glucose. The HMF yields reported from fructose (Table I) appear high, but do no concern isolated HMF, but rather calculated values on the basis of UV analysis. The yield of the ethers of 5-hydroxymethylfurfural is unknown, given the indication that the furfuryl alcohols were very unstable to acid and readily polymerised at room temperature, it is thus rather evident that the yield of such ethers is rather insignificant.

In the paper by Tarabanko et al, on the "Preparation of butyl levulinate by the acid-catalyzed conversion of sucrose in the presence of butanol", published in "Khimiya Rastitel'nogo Syrýa (2004), (2), 31-37, the pulse-flow process of the acid-catalyzed conversion of sucrose in the two-phase water-butanol system is studied. 5-HMF and levulinic acid were obtained as the main products, using a solution of sulphuric acid and sodium hydrosulfate as catalyst. The conversion of glucose into an alkoxymethylfurfural is not disclosed. A similar conclusion may be drawn on the second article by the same author: "Catalyzed carbohydrate dehydration in the presence of butanol at moderate temperatures", published in "Khimiya Rastitel'nogo Syrýa (2002), (2), 5-15

RU2203279 relates to the synthesis of 5-hydroxymethylfurfural ethers from sucrose. The end product is synthesized by dehydration of sucrose or fructose in a biphasic system in the presence of sodium bisulfite or mixture of sodium bisulfite and sulfuric acid as catalyst and aliphatic alcohols as alkylating agent under normal pressure. In a biphasic system, these catalysts are homogeneous. Another distinguishing feature of this process is the use of sucrose or fructose as the parent reagent.

Finally, WO9967409 relates to a "METHOD OF TREATING BIOMASS MATERIAL" wherein hemicellulosic and cellulosic components in biomass material are hydrolyzed in a single-stage digester by using a dilute mineral acid such as sulfuric acid or nitric acid, at a temperature above 200 DEG C and a residence time of less than ten minutes. The hemicellulosic components are converted to monosaccharides selected from the group consisting of pentoses and hexoses and the cellulosic components are converted to glucose. In addition, organic acids, furfural, 5-hydroxymethylfurfural, acid-soluble lignin, levulinic acid and other products are produced. The acid used is sulphuric acid or nitric acid, as a dilute aqueous solution, i.e., a homogeneous catalyst. The product stream is one of C6 and C5 sugars combined with furfural, HMF, levulinic acid, ASL and other extracted organics. The preparation of alkoxy ethers of HMF is not disclosed.

Concluding, the current methods for the synthesis of HMF mostly start from fructose and typically do not give high yield, partly attributable to the instability of HMF under the acidic reaction conditions. In most acid-catalysed water-based reactions, the further reaction to levulinic acid and humins has been reported, making this a less attractive alternative.

The present inventors have set out to overcome these disadvantages.

SUMMARY OF THE INVENTION

Surprisingly, the inventors have found that the conversion of hexose-containing starting material, in particular fructose and/or glucose-containing starting material and more particular glucose-containing material that may be derived from biomass in the presence of a catalytic or sub-stoechiometric amount of acid in the presence of an alcohol with or without the presence of one or more additional diluents leads to the formation of the corresponding HMF-ether in good yield and selectivity.

Thus, the invention pertains to a method for the manufacture of 5-alkoxymethylfurfural ethers by reacting a fructose and/or glucose-containing starting material with an alcohol in the presence of a catalytic or sub-stoechiometric amount of acid catalyst.

It was found that this in situ formation and derivatisation of HMF prevents the occurrence of the onward and undesired reaction towards the above-mentioned levulinic acid and humins, thus leading to an efficient procedure for the conversion of fructose and/or glucose-containing material into HMF derivatives.

The energy density of 5-ethoxymethylfurfural (EMF), the ether resulting from reaction of HMF with (bio)ethanol, can be calculated. Taking into account stoeichiometry and a calculated enthalpy of formation using increment tables of 502.32 kJ/mole, the reaction enthalpy can be calculated as 3854.76 kJ/mol, leading to an energy density of 7.0 kWh/kg or 8.7 kWh/L. This is as good as regular gasoline (12.7 kWh/kg, 8.8 kWh/L) and diesel kWh/kg, 9.7 kWh/L) and significantly higher than ethanol (7.7 kWh/kg, 6.1 kWh/L). This high energy density of EMF, the fact that these HMF derivatives can now be obtained in high yields, in one step, from very cheap hexose or hexose-containing starting materials such as sucrose and glucose, and as these ethers are, in contrast to HMF, liquids at room temperature, make these very interesting fuels or fuel additives.

In certain embodiments, the alcohol is selected from the group consisting of primary (un)branched aliphatic alcohols. In certain preferred embodiments, the alcohol is selected from the group consisting of primary C1-C5 (un)branched aliphatic alcohols, preferably methanol, ethanol, 1-propanol, 2-hydroxymethyl-propanol, 1-butanol. More preferable are methanol and/or ethanol. The resulting (m)ethyl ether ((m) ethoxymethylfurfural, MMF or EMF) has a high energy content and may directly be used as a fuel additive as an alternative for MTBE or as a fuel. Mixtures of alcohols may also be employed. Ethanol is the most preferred alcohol in the method of the present invention as the ethanol that is used can also be derived from biomass or glucose-containing material (bio-ethanol).

The acid catalyst in the method of the present invention can be selected from amongst solid (halogenated) organic acids, inorganic acids, salts, Lewis acids, ion exchange resins and zeolites or combinations and/or mixtures thereof, including combinations and/or mixtures thereof with a homogenous catalyst. The expression "solid" is here used in the ordinary meaning of the word as being solid during the reaction. Another common expression for solid catalysts is "heterogeneous" catalyst. The acid may be a protonic, Brønsted or, alternatively, a Lewis acid. In certain embodiment, the acid may be organic or inorganic. In certain embodiments, the organic acid can be selected from amongst oxalic acid, levulinic acid, maleic acid or para-toluenesulphonic acid. In certain embodiments, the inorganic acid can be selected from amongst phosphoric acid, sulphuric acid, hydrochloric acid, hydrobromic acid, nitric acid, hydroiodic acid, optionally generated in situ. In certain embodiments, the inorganic acid is selected form the group of sulphuric acid, phosphoric acid, hydrochloric acid, nitric acid. In certain embodiments, the salt can be one of $(NH_4)_2SO_4/SO_3$, ammonium phosphate, triethylamine phosphate, pyridinium salts, pyridinium phosphate, pyridinium hydrochloride/hydrobromide/perbromate, DMAP, aluminium salts, Th and Zr ions, zirconium phosphate, Cr-, Al-, Ti-, Ca-, In-ions, $ZrOCl_2$, $VO(SO_4)_2$, $TiO_2$, V-porphyrine, Zr-, Cr-, Ti-porphyrine. In certain embodiments, the Lewis acid can be one of $ZnCL_2$, $AlCl_3$, $BF_3$. In certain embodiments, the ion exchange resins can be one of Amberlite, Diaion, levatit. In certain embodiments, it is preferred that the acid catalyst is a solid catalyst that may be selected form the group consisting of acid resins, natural clay mineral, zeolites, supported acids such as silica impregnated with mineral acids, heat treated charcoal, metal oxides, metal sulfides, metal salts and mixed oxides and mixtures thereof. In certain embodiments, mixtures or combinations of acid catalysts can be used.

The temperature at which the reaction is performed may vary, but in general it is preferred that the reaction is carried out at a temperature from 50 to 300 degrees Celsius, preferably from 125 to 250, more preferably from 175 to 225 degrees Celsius. In general, temperatures higher than 300 are less preferred as the selectivity of the reaction as many by-products occur, inter alia caramelisation of the sugar. Performing the reaction below the lowest temperature is also less preferable because of the slow reaction speed.

The fructose and/or glucose-containing starting material can be selected from a wide variety of feeds. In general any feed with a sufficient high fructose or glucose content can be used. It is preferred that the fructose and/or glucose-containing starting material is selected from the group of starch, amylose, galactose, cellulose, hemi-cellulose, glucose-containing disaccharides such as sucrose, maltose, cellobiose, lactose, preferably glucose-containing disaccharides, more preferably sucrose or glucose.

The catalyst can be added to the reaction mixture in an amount varying from 0.01 to 40 mole % drawn on the fructose or glucose content of the fructose and/or glucose-containing starting material preferably from 0.1 to 30 mole %, more preferably from 1 to 20 mole %.

In certain embodiments, one or more solvents or diluents may be added, in general to aid the dissolution of the glucose containing material or as a diluent. The solvent may be selected form the group consisting of water, sulfoxides, preferably DMSO, ketones, preferably methyl ethylketone, methylisobutylketone and acetone or mixtures of two or more of the above solvents.

In certain embodiments, the ratio of alcohol/solvent is from 50 to 0.1, preferably from 20 to 1, more preferably from 10 to 2.

Higher amounts of alcohol may have the result that the reaction is too slow due to the limited solubility (hence availability of the starting material), whereas too much solvent in the system may lead to a too high dilution, which in both cases are less preferred results. One of the possible solvents is water.

In certain embodiments, the method can be performed in a continuous flow process. In such method, the residence time of the reactants in the flow process is between 0.1 second and 10 hours, preferably from 1 second to 5 hours, more preferably from 1 minute to 1 hour.

In certain embodiments the continuous flow process is a fixed bed continuous flow process or a reactive (catalytic) distillation process with preferably a solid ("heterogeneous") acid catalyst. To initiate or regenerate the heterogeneous acid catalyst or to improve performance, an inorganic or organic acid may be added to the feed of the fixed bed or reactive distillation continuous flow process. In a fixed bed process, the liquid hourly space velocity (LHSV) can be from 1 to 1000, preferably from 5 to 500, more preferably from 10 to 250 and most preferably from 25 to 100.

As explained above, the application of the products of the method of the present invention, i.e. the ethers, is in the use as a fuel or fuel additive and as precursor for the manufacture of 2,5-di(hydroxymethyl)furan, furan-2,5-dicarboxylic acid, 2-hydroxymethylfuran-5-carboxylic acid, 2,5-(dihydroxymethyl)tetrahydrofuran, which can be used as monomers in a polymerisation process, optionally after conversion of the diol to a diamine. See for a review Moreau, Topics in catalysis, 2004, 27, 11-30.

DETAILED DESCRIPTION OF PREFERRED EMBODIMENTS

Examples

Apparatus

Figure 1A:
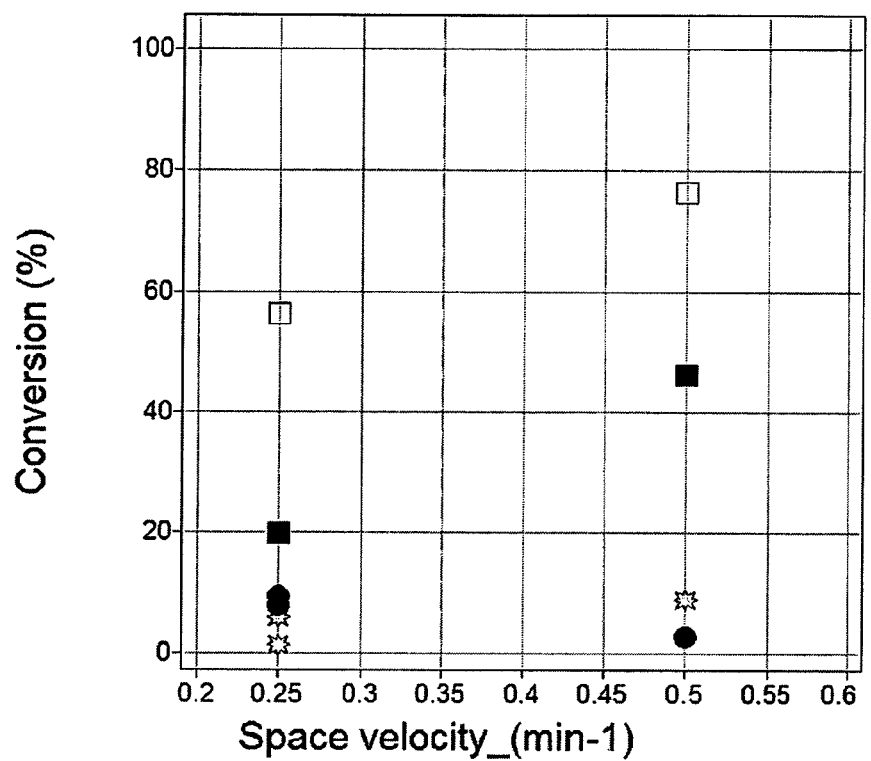
FIG. 1. Plot of a) conversion, b) selectivity to furan derivatives versus space velocity. 180 C, heterogeneous catalysts, reaction medium water. Catalyst 1: ☐; Catalyst 2: ■ Catalyst 3: * Catalyst 4: ●.

Continuous parallel flow reactor system consisting of four quartz reactors inserted in a silver heating block; temperature and flow regulators and three HPLC pumps. Two of the pumps deliver the liquid to the reactors and third one is employed to dilute the reaction products prior to collection.

Analytical Method

The reaction products were quantified with the aid of HPLC-analysis with an internal standard (saccharine, Sigma Aldrich). A Merck-Hitachi L7000 chromatograph, equipped UV and RI detectors, was used. Stationary phase were reverse phase C18 (Sunfire 3.5 ☐m, 4.6×100 mm, Waters) and cation exchange (SupelcogelH, 4.6×300 mm, SigmaAldrich) columns connected in series. A gradient elution at a constant flow 0.6 ml/min and temperature 60° C. was used according to the following scheme.

| Time (min) | 0.2% TFA (aq) | Methanol | Acetonitrile |
|---|---|---|---|
| 0 | 90.0 | 7.0 | 3.0 |
| 10 | 90.0 | 7.0 | 3.0 |
| 11 | 80.0 | 0.0 | 20.0 |
| 15 | 80.0 | 0.0 | 20.0 |
| 16 | 90.0 | 7.0 | 3.0 |
| 21 | 90.0 | 7.0 | 3.0 |

General Procedure

A 1.25 wt % solution of glucose (99.7% Sigma Aldrich) in water or 88.7% ethanol was flowed through a fixed bed (200 ☐l) of a solid ("heterogeneous") catalyst at 180° C. Flow rates were chosen such to achieve a space velocity 0.25 or 0.5 $min^{-1}$, i.e. contact time 2 or 4 min. Liquid coming out of the reactors was diluted by a mixture of water and ethanol (50:50) to prevent tubing blockages.

Catalysts Tested:
Catalyst 1 Zeolite beta SAR25 (CBV Zeolyst)
Catalyst 2 Zeolite Y high SAR (CBV Zeolyst)
Catalyst 5 Mordenite H SAR 90 (CBV Zeolyst)
Catalyst 7 Zeolite Y SAR 5.17 (CBV Zeolyst)

Contact time and space velocity were calculated as follows:

$$Sv = Fr_{feed}/V_{cat}$$

Sv space velocity ($min^{-1}$)
$Fr_{feed}$ flow rate feed (ml/min)/
$V_{cat}$ catalyst volume (ml)

$$t_c = 1/Sv$$

$t_c$ contact time (min)

Conversion of substrate, selectivity and yield of furan derivatives were calculated according to the following formulae:

$$X = 100 * m_{r\ substrate}/m_{0\ substrate}$$

X conversion (%)
$m_{r\ substrate}$ amount of reacted substrate (mg)
$m_{0\ substrate}$ amount of substrate in feed (mg)

$$S_{compound} = 100 * n_{r\ substrate}/n_{0\ substrate}$$

$S_{compound}$ selectivity to compound (%)
$n_{r\ substrate}$ moles of substrate reacted
$n_{0\ substrate}$ moles of substrate in feed $$Yield = 100 * n_{product}/n_{0\ substrate}$$

Yield yield (%)
$n_{product}$ moles of product formed

Catalysts Tested:
Catalyst 1 Zeolite beta SAR25 (CBV Zeolyst)
Catalyst 2 Zeolite Y high SAR (CBV Zeolyst)
Catalyst 3 Mordenite H SAR 90 (CBV Zeolyst)
Catalyst 4 Zeolite Y SAR 5.17 (CBV Zeolyst)

Reactions in Water.

Figure 1B:
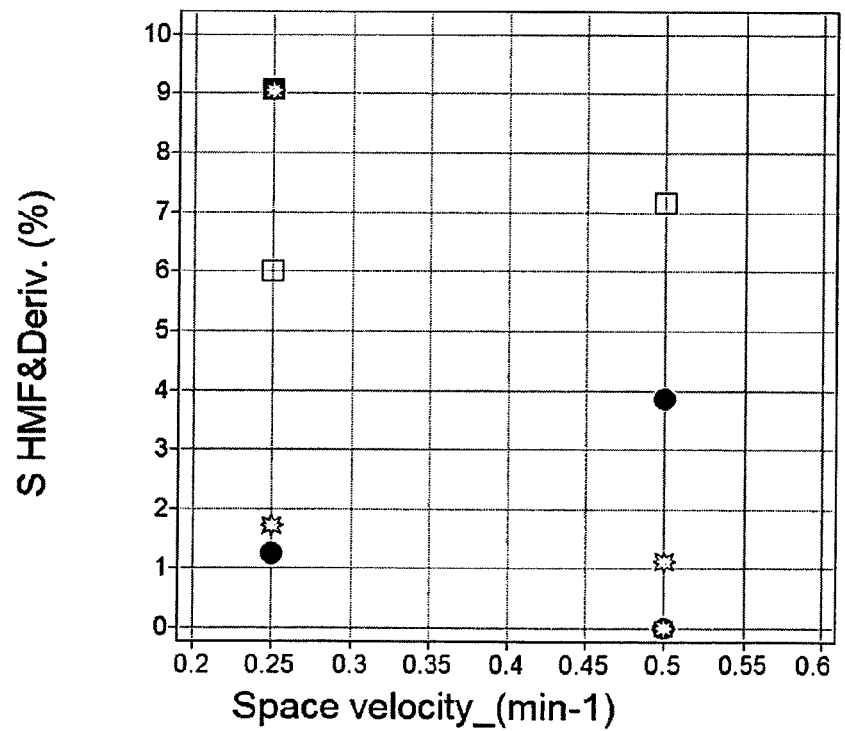
Figure 2A:
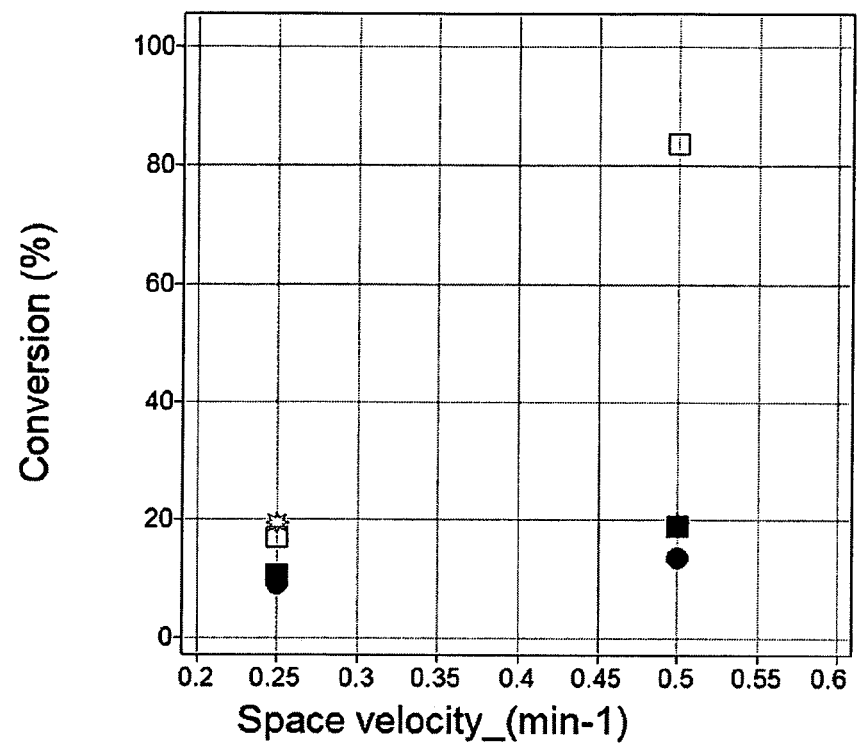
FIG. 2. Plot of a) conversion, b) selectivity to furan derivatives versus space velocity. 180 C, heterogeneous catalysts, reaction medium 88.7% ethanol. Catalyst 1: ☐; Catalyst 2: ■ Catalyst 3: * Catalyst 4: ●.
Figure 2B:
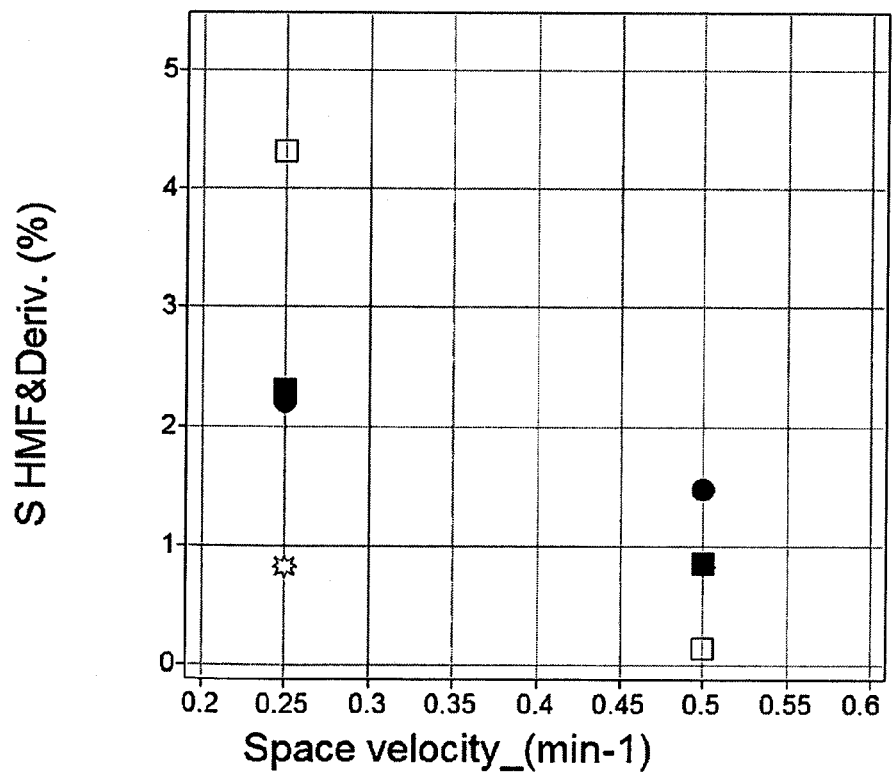

FIGS. 1 a) and b) show that a conversion achieved for the catalysts tested was 76% (Zeolite beta). This catalyst gave 7% selectivity to HMF and EMF.

Zeolite Y with high SAR presented 9% selectivity to furans at 20% conversion. Y zeolite with low SAR (catalyst 4) shows selectivity of 4% at very low conversion. Mordenite presented both reduced activity and selectivity to furan derivatives.

HMF was a main furan found in the reaction mixture.

Reactions in Ethanol.

With the use of Zeolite beta about 4% selectivity to HMF and EMF was achieved at 17% conversion at a low space velocity. For the other catalysts tested, the conversion developed initially to more than 20% and the selectivity was in the range between 1 and 3%.

The predominant furan derivative was the desired EMF.

DATA Fructose + Ethanol with solid acid catalyst 1
fructose conc 55.5 mmol/L; 90% EtOH

| Res time/s | fructose conversion % | Y (HMF) % | Y (EMF) % | S (HMF) % | S (EMF) % |
|---|---|---|---|---|---|
| 10 | 42 | 2 | 9 | 5 | 21 |
| 30 | 76 | 3 | 24 | 4 | 32 |
| 60 | 93 | 1 | 35 | 1 | 38 |
| 120 | 98 | 1 | 37 | 1 | 38 |

DATA Glucose + Ethanol with solid acid catalyst 1
glucose conc 55.5 mmol/L; 90% EtOH

| Res time/s | glucose conversion % | Y (HMF) % | Y (EMF) % | S (HMF) % | S (EMF) % |
|---|---|---|---|---|---|
| 60 | 73 | 2 | 23 | 3 | 32 |
| 180 | 92 | 1 | 23 | 1 | 25 |
| 300 | 97 | 1 | 24 | 1 | 25 |
| 600 | 98 | 1 | 22 | 1 | 22 |

DATA Sucrose + Ethanol with solid acid catalyst 1
sucrose conc 27.8 mmol/L (55.5 mmol/L C6H12O6); 90% EtOH

| Res time/s | Glu + fru Conversion % | Y (HMF) % | Y (EMF) % | S (HMF) % | S (EMF) % |
|---|---|---|---|---|---|
| 60 | 86 | 4 | 22 | 5 | 26 |
| 180 | 96 | 3 | 26 | 3 | 27 |
| 300 | 98 | 3 | 28 | 3 | 29 |
| 600 | 99 | 2 | 27 | 2 | 27 |

Engine Test

In a small-scale model diesel engine, comparative testing is performed with normal commercial diesel as a fuel and the same commercial diesel to which samples of 1 wt. %, 2 wt. %, 3 wt. %, 5 wt %, and 10 wt. % HMF or EMF are added, respectively. The diesel samples with HMF are less homogenous on visual inspection (solid particles remain visible, flocculation) and above 5 wt. % HMF, a solid deposit is sometimes observed. EMF is added as a liquid and does not yield any mixing or flocculation problems. The engine is run stationary with a set volume (100 mL) of fuel until empty. HMF containing fuels run less regular, whereas EMF containing fuels run at a regular pace and for a longer period (up to 15%). On visual inspection of the engine, EMF provides less visual contamination.

What is claimed is:

1. A fuel comprising 5-alkoxymethylfurfural, wherein the fuel is selected from the group consisting of gasoline and diesel.

2. A fuel additive for a fuel comprising 5-alkoxymethylfurfural, wherein the fuel is selected from the group consisting of gasoline and diesel.

* * * * *